United States Patent [19]

Cantrell

[11] Patent Number: 5,107,046
[45] Date of Patent: Apr. 21, 1992

[54] PROCESS FOR PREPARING AROMATIC FLUORIDES

[75] Inventor: Gary L. Cantrell, Troy, Ill.

[73] Assignee: Mallinckrodt Specialty Chemicals Co., Inc., St. Louis, Mo.

[21] Appl. No.: 527,796

[22] Filed: May 23, 1990

[51] Int. Cl.$^5$ .................. C07C 17/22; C07C 25/13; C07C 215/38; C07C 211/72
[52] U.S. Cl. .................... 570/141; 534/565; 546/159; 546/304
[58] Field of Search .............. 570/141; 534/565; 546/159, 304

[56] References Cited

U.S. PATENT DOCUMENTS

| | | | |
|---|---|---|---|
| 4,075,252 | 2/1978 | Boudakian | 260/649 F |
| 4,092,306 | 5/1978 | Eastlick | 534/565 |
| 4,096,196 | 6/1978 | Boudakian | 260/650 F |
| 4,886,920 | 12/1989 | Cantrell | 570/141 |

FOREIGN PATENT DOCUMENTS

| | | |
|---|---|---|
| 258985 | 10/1986 | European Pat. Off. . |
| 0330420 | 2/1989 | European Pat. Off. . |
| 2173188 | 2/1986 | United Kingdom . |
| 07987 | 10/1988 | World Int. Prop. O. ......... 534/565 |

OTHER PUBLICATIONS

Olah et al., *J. Org. Chem.*, 44(22) (1979).
Yoneda, *Synthetic Communications*, 19:865-871 (1989).
"An Improved Procedure for Diaotization Fluoro-Dediazoniation of Anilines Using Organic Base-HF Agents", Synthetic Communications 17 (6), 685-692 (1987).
"Heterolytic Dediazoniation of Benzenediazonium Ions . . .", Journal of the American Chemical Society, 97:1, Jan. 8, 1975, Olah et al.
Kollonitsch, "Antiprotozal 2-flurophenyl-4(5)-nitroimidazoles," Chemical Abstracts, 71:70002 (1964).

*Primary Examiner*—J. E. Evans
*Attorney, Agent, or Firm*—Rothwell, Figg, Ernst & Kurz

[57] ABSTRACT

An improved process is disclosed for preparing aromatic fluorides by diazotization-fluorination in hydrogen fluoride. The improvement includes, prior to the decomposition of the diazonium fluoride, adding to the diazotizing reaction mixture, urea or a salt thereof in an amount sufficient to reduce the vapor pressure of hydrogen fluoride over the diazonium solution. Also disclosed is a process for reducing the vapor pressure over diazonium fluoride solutions.

14 Claims, No Drawings

PROCESS FOR PREPARING AROMATIC FLUORIDES

FIELD OF THE INVENTION

This invention relates to an improved process for preparing aromatic fluorides from aromatic amines by means of diazotization-fluorination reactions in hydrogen fluoride.

BACKGROUND OF THE INVENTION

Preparation of aromatic fluorides from corresponding aromatic primary amines by a diazotization-fluorination process is well known. In such processes, an aromatic primary amine is diazotized in a reaction mixture comprising (i) a reaction medium consisting essentially of hydrogen fluoride, (ii) the amine and (iii) a nitrosonium ion-containing or—generating diazotization agent under reaction conditions such that the resulting reaction mixture comprises an aromatic diazonium fluoride. The aromatic diazonium fluoride then is decomposed at elevated temperature in the resulting reaction mixture to nitrogen and the corresponding aromatic fluoride.

Generally, as is illustrated in U.S. Pat. No. 4,075,252, this decomposition step occurs by heating the reaction mixture to the decomposition temperature. The decomposition temperature is that temperature at which nitrogen evolution from the reaction mixture becomes substantially complete. Usually, as the reference discloses, nitrogen evolution will have been completed by the time the temperature reaches the reflux temperature of the reaction mixture. In those instances where higher temperatures are required, they can be obtained either by heating under pressure or evaporating solvent until the desired temperature is reached. U.S. Pat. No. 4,075,252 discloses the addition of ammonium salts to lower the reflux temperature.

U.S. Pat. No. 4,096,196, discloses the inclusion of tertiary amines in a diazotization reaction medium. This reference does not state how the addition of tertiary amine compounds aids the diazotization-fluorination reaction. Olah, et al., *J. Org. Chem.*, Vol. 44, No. 22, 1979, discloses the use of pyridine in an HF solution (pyridinium poly(hydrogen fluoride) reagent) rather than pure HF as a fluorinating agent.

Yoneda, *Synthetic Communications*, 19:865-871 (1989) discloses the preparation of aromatic fluorides via diazotization in anhydrous hydrogen fluoride—organic base solutions.

European Patent Application 0330420 discloses a process for the manufacture of fluoroaromatics which consists of feeding an aromatic amino in the presence of HF to a reaction zone simultaneously with a diazotizing agent so as to effect diazotization of the aromatic amine, thermally decomposing the resulting diazonium salt substantially as it is formed, and removing the resulting fluoroaromatic compound from the reaction zone substantially as it is formed. The amine and the diazotization agent are fed to the reaction zone in such quantities and proportions that they are consumed substantially as fed so that no substantial concentration of either builds up in the reaction zone. A preferred embodiment discloses the addition of ammonium ions to the reaction mixture.

The use of urea as a nitrosonium scavenger in diazotization reactions is disclosed in U.S. patent application Ser. No. 151938, filed Feb. 3, 1988, incorporated herein by reference. Urea is not a nitrosonium scavenger in HF systems.

The heretofore known processes for preparing fluoroaromatic compounds via decomposition of corresponding aromatic diazonium fluorides have not been entirely satisfactory in that they typically are complex, inefficient, expensive, and/or prone to result in an unexceptably high level of tar and/or other by-products. Accordingly, there is a substantial need in the art for a diazonium fluoride decomposition process which would overcome these disadvantages. There is also a need for a process for decomposing aromatic diazonium fluorides which provides for the optimization of yield with the minimization of undesired by-products and avoids unnecessary safety hazards.

SUMMARY OF THE INVENTION

It now unexpectedly has been found that the addition of urea to a reaction medium consisting essentially of hydrogen fluoride and diazotization products suppresses the vapor pressure of hydrogen fluoride over the diazotization solution so that the dediazoniation can be carried out at a temperature higher than the normal reflux temperature of the hydrogen fluoride solution. Generally stated, therefore, the present invention provides an improvement in the above described, heretofore known diazotization-fluorination processes wherein a diazotized reaction mixture comprises an aromatic diazonium fluoride in hydrogen fluoride. The improvement comprises adding urea to the reaction mixture. Urea is added in an amount effective to suppress the vapor pressure of hydrogen fluoride over the diazotization solution.

Aromatic fluorides prepared by the improved process of the present invention are useful as intermediates for preparing a variety of end-products, including, for example, various pesticides, herbicides, and pharmaceuticals such as tranquilizers and the like.

DETAILED DESCRIPTION OF THE INVENTION

In the initial step of the preferred process of this invention, there is formed a liquid amine-hydrogen fluoride solution comprising liquid hydrogen fluoride (HF) and, dissolved therein, the particular aromatic primary amine to be diazotized to the corresponding aromatic diazonium fluoride. In keeping with well known techniques for handling HF, the solution is preferably formed in a vessel having internal surfaces which are resistant to degradation by hydrogen fluoride. Such an appropriate reaction vessel would have surfaces which were formed, for example, of stainless steel or, preferably, teflon.

The aromatic amine is added with stirring to sufficient liquid HF to prepare an amine-HF solution wherein the resulting dissolved amine remains dissolved at 0° C. The process of the present invention can be used for all aromatic amines which are diazotizable under HF acid conditions. Such diazotizable aromatic amines include diazotizable carbocyclic aromatic primary amines (e.g. amino-benzenes) and heterocyclic aromatic amines (e.g. amino-pyridines), including heterocyclic aromatic primary amines containing structures wherein benzene is condensed with a heterocyclic ring. Such amines include carbocyclic and heterocyclic monoamines and carbocyclic and heterocyclic polyamines (e.g. diamines). Included, for example, are amines derived from such carbocyclic aromatic compounds as benzene, biphenyl, diphenylmethane, diphenyl ether, condensed benzenoids such as naphthalene and anthracene, and from such heterocyclic aromatic compounds as pyridine, quinoline and isoquinoline. The aromatic ring or rings in the aromatic amines may be unsubstituted or substituted with one or more substituents selected from the group consisting of alkyl (e.g. linear or branched alkyl having 1 to 12, preferably 1 to 4, carbon atoms), alkoxy (e.g. linear or branched alkoxy having 1 to 12, preferably 1-4, carbon atoms), halo (e.g., chloro, fluoro and bromo), nitro, cyano, acyl (e.g. linear or branched acyl having 1-4 carbon atoms, such as acetyl), acylamino (e.g. acetylamino), carboxy and hydroxy groups.

Suitable carbocyclic aromatic primary amines include, for example, aniline; methoxyaniline (e.g., para-anisidine); chloroaniline and bromoaniline in which the chloro or bromo group is in the ortho, meta or para position relative to the amine group; toluidines such as ortho-, meta- and para-aminotoluene; and ring-halogenated (e.g., ring-chlorinated or ring brominated) derivatives of such toluidines, e.g., 2-chloro-6-aminotoluene (also called 6-chloro-ortho-toluidine); ortho-, meta- and para-phenylene diamine; methylene dianilines such as 3,3'-, 4-4,' and 3,4'-methylene dianiline; biphenyl amines, (e.g. 3,3'-diamino-biphenyl, 4,4'-diamino-biphenyl and 3,4'-diamino-biphenyl). Suitable heterocyclic aromatic primary amines include, for example, 2-, 3- and 4-aminopyridine; diaminopyridines such as 2,6-diaminopyridine; haloaminopyridines such as 2-amino-4-, 5- and 6-chloropyridine and 3-amino-5- and 6-chloropyridine; nitroaminopyridines such as 2-amino-5-nitro-pyridine; and alkylaminopyridines such as 2-amino-4-, 5- and 6- methylpyridine and 2-amino-4,6-dimethylpyridine.

In a preferred embodiment of this invention, the aromatic amine is 3-chloro-4-fluoroaniline and the resulting diazotized amine is 3-chloro-4-fluorobenzene diazonium fluoride, which can be decomposed to form 1-chloro-2,5-difluorobenzene, which is useful as an intermediate for preparing herbicides and pharmaceuticals.

As indicated above, the amine is dissolved in a sufficient amount of HF such that the amine remains dissolved at 0° C. Such an amount of HF is approximately 5-15 moles of HF per mole of amine, when the amine is 3-chloro-4-fluoroaniline. The corresponding amounts for other amines can be readily determined by those skilled in the art. Optionally, the HF can contain ammonium ions which may increase the product yield.

A diazotization agent which contains or forms the nitrosonium ion is added with stirring to sufficient liquid HF to prepare a solution of nitrosyl fluoride in HF wherein the dissolved agent remains dissolved at 0° C. Suitable diazotization agents include, for example, alkali metal nitrites (e.g., sodium nitrite and potassium nitrite), nitrous halide, dinitrogen trioxide, nitrous oxide, nitrous acid and nitrous anhydride. Sodium nitrite is preferred. An amount of HF corresponding to a ratio of at least 12 moles of HF per mole of sodium nitrite has been found sufficient. Sufficient amounts of HF for other diazotization agents can readily be determined by those skilled in the art. Alternatively, the diazotization agent can be added directly to the solution of aromatic amines in HF. The above described portion of the process of the present invention is based on the chemical reaction represented by the following illustrative equation:

$$Ar(NH_2)_m + 2mHF + mNaNO_2 = Ar(N_2^+)_m(F^-)_m + mNaF + 2mH_2O$$

where Ar is an aromatic moiety of the aromatic mono- or polyamine $Ar(NH_2)_m$, $m = m$ and is an integer of 1, 2 or more and preferably is 1 or 2, and $NaNO_2$ illustrates the diazotization agent.

Hydrogen fluoride acts both as a reactant (e.g., a source of fluorine for the aromatic diazonium fluoride being prepared) and as the medium for the diazotization reaction. In order to serve as the reaction medium, there is employed an amount of HF in excess of the amount of HF required for use as such reactant. The amount of HF employed in each solution is preferably such that the total amount of HF in the amine-HF solution and nitrosyl fluoride solution introduced into the reactor results in introduction of from about $(3+m)$ to about 30 moles and preferably from about $(15+m)$ to 20 moles of HF per mole of introduced amine where m is the number of diazotizable-$NH_2$ per molecule of the amine. In general, amounts of HF greater than $(3+m)$ moles per mole of amine are needed to solubilize the arylamine at the diazotization temperature. Amounts of more than 30 moles of HF per mole of amine generally result in unacceptably slow preparation of aromatic diazonium fluoride and/or unacceptable high cost of HF recovery. The hydrogen fluoride may be added as aqueous hydrofluoric acid containing, for example, from about 3 to about 30 or more percent by weight of water, preferably containing at least 70 percent by weight of HF (dry basis). However, better yields and greater freedom from tar, phenols and other by-products and subsequent decomposition of the diazonium fluoride to the aromatic fluoride can be obtained by employing at least substantially anhydrous hydrogen fluoride, i.e., not containing more than about 2% by weight water.

The HF solution of diazotization agent is added with stirring to the HF-amine solution at a sufficiently slow rate and with sufficient cooling of the resulting reaction mixture such that the temperature of the reaction mixture is maintained from about $-10°$ C. to about $10°$ C. Alternatively, the diazotization agent may be added directly to an HF-amine solution. However, such solution should contain all the HF desired to be used. The time required for addition of the diazotization agent depends on cooling capacity and rate of diazotization. In general, such addition can be completed in from 10 minutes or less to 10 hours or more without exceeding the temperature limitation. In general, the diazotization reaction proceeds to completion within a short time (e.g. 0.5 to 2 minutes) after completion of addition of the diazotization agent. The reaction rate is temperature and concentration dependent such that a low temperature and low concentration may give a slower reaction rate and may result in incomplete diazotization.

Inasmuch as a nitrosonium-ion oxidizing agent has deleterious effects on the decomposition products of diazonium fluoride, the reaction mixture should be tested for presence of oxidizing agents. If present, e.g. by virtue of excess addition of diazotization agent, contacting a sample of the reaction mixture with filter paper impregnated with a mixture of starch and potassium iodide will result in a characteristic dark blue spot on the test paper. Should oxidizing agents be present, they can be decomposed in accordance with the method disclosed in U.S. Pat. No. 4,886,920 incorporated herein by reference.

Urea is added to the reaction mixture. The urea can be added after the diazotization is complete. Alternatively, the urea can be added prior to the diazotization, being mixed together with the amine/HF solution either by itself or in HF solution. Less desirably, the urea can be mixed with HF and the resulting solution then mixed with the diazotization agent prior to reacting with the amine. If this alternative is selected, the urea/HF solution should be diluted to prevent the urea from destabilizing the diazotization agent. If the diazotization agent is destabilized, it can precipitate, an undesirable occurrence. It has been found that dry urea desirably should not be mixed with the diazotization agent. Doing so causes undesirable reactions to occur on the surface of the urea particles. Preferably, urea is added after the addition of the diazotization agent, preferably sodium nitrite.

The addition of urea and/or its salts as an additive to the diazonium/HF solution generally acts to increase the reflux temperature of the reaction mixture without reducing the fluoroaromatic yield resulting after decomposition. The use of urea dramatically reduces the vapor pressure over the diazotization solution, in some cases eliminating the need for super-atmospheric pressure in the decomposer. The reduction of vapor pressure is desirable in that a reaction which would otherwise require higher applied pressures to be driven can proceed under safer conditions, i.e., lower applied pressures.

Urea can be used in batch or continuous processes. In continuous processes the urea can be added continuously or incrementally. In batch processes the urea can be added at one time or incrementally. The urea is added in increments to a stirred diazonium/HF solution which is being maintained at about 25° C.; a preferred ratio of urea addition is about one pound of urea per 25 gallons solution per minute. The amount of urea which is added can vary depending upon the aromatic fluoride product to be obtained, but should be a sufficient amount to reduce the vapor pressure of the hydrogen fluoride above the diazonium solution without having a substantial effect on the yield following decomposition of the diazonium fluoride. This amount can readily be determined by those of skill in the art.

To determine the amount of urea to be added, the effect of urea on the vapor pressure of a synthetic HF heel at a desired stoichiometry, for example 1 mole of amine per X moles of HF where X is selected as desired, is calculated. A curve of the urea concentration versus the HF pressure over the synthetic heel is plotted. The target pressure for a given reaction is determined by the type of equipment used and is based on safety concerns. The rate of decomposition for a particular diazonium salt at a particular temperature is generally known to, or can be calculated by, a practitioner of ordinary skill in the art. Knowing the target pressure and the rate of decomposition permits the determination of the desired HF pressure in the decomposer. The urea concentration to be used in a particular reaction can then be determined from the urea concentration - HF pressure curve.

In general, the use of up to approximately 11 weight percent, preferably about 9 weight percent, of urea will have a minimal effect on yield. The use of greater amounts of urea will cause some product to be retained in the HF heel. While not wishing to be bound by theory, it is believed that this retention is due to a poor phase separation after decomposition is completed and increased entrainment of product in the urea-HF phase.

Product which remains in the HF-heel subsequently can be recovered by extraction with a suitable solvent of the type known to those of skill in this art. Suitable solvents would include, for example, methylene chloride.

After the addition of urea, the dediazoniation can be carried out either in a batchwise or continuous manner. The dediazoniation rate is dependent upon the temperature of the decomposition mixture and the stability of the particular aromatic diazonium fluoride. Generally, the higher the decomposition temperature, the faster the rate of nitrogen evolution and the higher the HF vapor pressure. Higher HF vapor pressures result in larger HF losses. Urea lowers the HF vapor pressure at higher temperatures, thereby lowering HF losses. Usually, dediazoniation is not carried out under complete containment, but the nitrogen is vented off during the reaction.

The resulting aromatic fluoride product conveniently can be recovered from the reaction mixture by decanting the organic phase directly with or without a co-solvent, and distilling or steam distilling the aromatic fluoride after neutralization.

As an alternative, an aromatic amine and a diazotizing agent can be fed simultaneously into a reaction zone containing HF. In this instance, urea will have previously been introduced into the HF. Preferably, the reaction zone will be at a temperature sufficient to effect decomposition of the resulting diazonium fluoride. The decomposition temperature can be calculated in advance and is dependent upon the particular fluoroaromatic desired. Preferably, the amine and diazotizing agent are added in quantities and proportions which prevent the build-up of a substantial concentration of either the amine or agent. Preferred proportions would be stoichiometric proportions. When the temperature is such as to effect decomposition of the diazonium fluorides, they will be decomposed substantially as soon as they form. The resultant fluoroaromatic can be removed from the reaction zone substantially as soon as it is formed. Suitable methods for such removal are known to those of skill in the art and include, for example, flashing or evaporation. Flashing can be effected by the heat evolved from the diazotization-decomposition steps. Optionally, the HF solution can contain, in addition to the urea, other compounds, such as ammonium ions. The urea serves its previously described functions. As described in EP 0330420, incorporated herein by reference, the presence of ammonium ions in the reaction zone increases the yield.

Practice of the present invention is further illustrated by the following non-limiting examples. All parts and percentages given throughout this disclosure including the examples and claims, are by weight unless otherwise indicated.

EXAMPLE 1

To an ice cooled polyethylene bottle were added 89.0 g (4.45 moles) of anhydrous hydrogen fluoride (HF). Crystals of 3-chloro-4-fluoroaniline (43.10 g, 0.293 mole, 99% purity) were added to the stirred HF in increments at a rate so as to minimize HF vaporization. The resulting final anilinium/HF solution weighed 131.33 g. Granular sodium nitrite was weighed (20.18 g, 0.2912 mole) and added in increments to the well-stirred, ice cooled 3-chloro-4-fluoroanilinium/HF. The temperature was maintained below 30° C. The resulting dark green diazonium/HF solution weighed 146.71 g. A 0.1 mL sample of this solution was diluted into 1 mL of deionized water. KI/starch indicator paper gave no positive test for remaining nitrite. Urea (prill) (15.08 g, 0.251 mole) was added in increments of 0.5 to 1 gram to the stirred diazonium/HF solution at 25° C. The urea was initially soluble but on addition of the final increments a suspension of finely dispersed particles resulted. No decomposition was apparent throughout the addition. The final diazonium suspension weighed 161.79 g. Of this, 156.0 g were poured into a 450 mL Parr reactor. The dediazoniation was carried out with no mixing by thermal initiation of the exothermic reaction under total containment of the evolved nitrogen. The thermal maximum recorded was 158° C. The reactor was cooled in a water bath to about room temperature before the nitrogen was slowly vented. The Parr reactor was sealed and reheated to obtain the approximate vapor pressure of the combined crude phases at given temperatures. The pressure was read directly from a 0–100 p.s.i. gauge, and the temperature from a 1/16" J-thermocouple in the reactor connected to a digital display. The reactor was heated in a mantle above the temperature range of interest and then allowed to air cool slowly. The appropriate vapor pressure at given temperatures is set forth below.

| Temperature (°C.) | Pressure (p.s.i.g.) |
|---|---|
| 115° C. | 21 |
| 110 | 20 |
| 105 | 19 |
| 90 | 17 |

The reactor was cooled to room temperature in a water bath. The contents were poured into a plastic separatory funnel. The dark green bottom HF phase weighed 93.23 g. The upper brown crude organic phase weighed 41.10 g. The organic crude was poured into 90 mL of 10% NaOH. The product co-distilled with water at about 90° C., forming a separate, colorless, bottom phase in the distillate receiver. The colorless product, 1-chloro-2,5-difluorobenzene, was dried over anhydrous magnesium sulfate and weighed 31.35 g (0.209 mole at 99% purity). The minimum yield therefore from the amount of diazonium/HF transferred was 73.8%. The term minimum is used because the HF phase was not analyzed. Additional product could be isolated from that phase, which would increase the yield.

EXAMPLE 2

The same general procedure was followed as in the previous sample except no urea was added. The 3-chloro-4-fluoroanilinium HF solution was made up by adding 66.8 g (0.454 moles at 99% purity) of 3-chloro-4-fluoroaniline to 120 g (6.00 moles) of anhydrous hydrogen fluoride. To the resulting well stirred solution was added, in small increments, 31.30 g (10.453 moles) of sodium nitrite. An additional charge of anhydrous hydrogen fluoride (14.05 g, 0.702 mole) to the 205.48 g of diazonium/HF solution was necessary in order to solubilize some suspended salt. 215.29 g of the diazonium solution was transferred into the 450 mL parr reactor (for a 2% transfer loss of 0.1055 g). The dediazoniation was exothermic to a maximum temperature of 178° C. The reactor was cooled to 30° C. and slowly vented. The organic and HF phases were separated in a plastic separating funnel and weighed into tared polyethylene bottles. The HF phase weighed 131.81 g and the organic phase 65.56 g. Both phases were added back to the reactor and heated above the temperature range of interest. The autoclave and contents were allowed to slowly air cool. The temperature and pressure readings were taken as before.

| Temperature (°C.) | Pressure (p.s.i.g.) |
|---|---|
| 115.0° | 68 |
| 110.0 | 62 |
| 105.0 | 56 |
| 102.5 | 52 |
| 100.0 | 48 |
| 95.0 | 44 |
| 90.0 | 40 |
| 23.0 | 6 |

The reactor was opened and the contents again separated. The organic phase was poured into excess 10% NaOH and the resulting brown heterogeneous solution distilled. The two phase distillate was collected in a 125 mL separatory funnel. The colorless 1-chloro-2,5-difluorobenzene (bottom phase) was separated, dried and weighed. The weight of the product was 51.53 g (0.347 mole) for a percent yield of 78%.

BEST MODE CONTEMPLATED

The best mode contemplated for carrying out this invention has been set forth in the above description, for example, by way of setting forth preferred materials and operating condition, including but not limited to preferred ranges and values of amounts and other nonobvious variables material to successfully practice of the invention in the best way contemplated at the time of executing this patent application.

It is understood that the foregoing detailed description is given merely by way of illustration and that many modification may be made therein without departing from the spirit or scope of the present invention.

What is claimed:

1. In a diazotization-fluorination process for preparing an aromatic fluoride from a corresponding diazotizable aromatic primary amine wherein in an appropriate reaction vessel (a) the amine is diazotized in a reaction mixture comprising (i) a reaction medium consisting essentially of hydrogen fluoride (ii) said amine and (iii) a nitrosonium ion-containing or generating diazotizing agent under reaction conditions such that the resulting reaction mixture comprises the resulting aromatic diazonium fluoride, and (b) the resulting aromatic diazonium fluoride is decomposed at elevated temperature in said resulting reaction mixture to nitrogen and the aromatic fluoride, the improvement which comprises adding urea to said reaction mixture in an amount equal to about 11 weight percent of said reaction mixture prior to decomposing the aromatic diazonium fluoride.

2. In a diazotization-fluorination process for preparing an aromatic fluoride from a corresponding diazotizable aromatic primary amine wherein in an appropriate reaction vessel (a) the amine is diazotized in a reaction mixture comprising (i) a reaction medium consisting essentially of hydrogen fluoride (ii) said amine and (iii) a nitrosonium ion-containing or generating diazotizing agent under reaction conditions such that the resulting reaction mixture comprises the resulting aromatic diazonium fluoride, and (b) the resulting aromatic diazonium fluoride is decomposed at elevated temperature in said resulting reaction mixture to nitrogen and the aromatic fluoride, the improvement which comprises adding urea to said reaction mixture in an amount equal to about 9 weight percent of said reaction mixture prior to decomposing the aromatic diazonium fluoride.

3. The process of claim 2, further comprising recovering said aromatic fluoride.

4. The process of claim 3, wherein said recovery step includes extracting said aromatic fluoride from said reaction vessel with a solvent.

5. The process of claim 4, wherein said solvent is methylene chloride.

6. A process for reducing the vapor pressure over a diazonium fluoride solution in a reaction vessel comprising adding to said solution urea in an amount equal to about 11 weight percent of said solution.

7. A process for reducing the vapor pressure over a diazonium fluoride solution in a reaction vessel comprising adding to said solution urea in an amount equal to about 9 weight percent of said solution.

8. A process for preparing fluoroaromatic compounds comprising:
(a) feeding to a reaction zone in a suitable reactor containing a solution of HF having urea dissolved therein, in an amount effective to reduce the vapor pressure over said HF solution, an aromatic amine and a diazotizing agent, said reaction zone having previously been heated to a temperature sufficient to effect a decomposition, said amine and said agent being fed to said zone in proportions and quantities such that no substantial concentration of either build up in said zone and such that diazonium fluorides form,
(b) decomposing said diazonium fluorides such that fluoroaromatic compounds are produced, and
(c) recovering said fluoroaromatic compounds from said reaction zone.

9. The process of claim 8, wherein said decomposition occurs substantially as said diazonium fluorides form.

10. The process of claim 9, wherein said recovery occurs substantially as said fluoroaromatics are produced.

11. The process of claim 10, wherein said amine and said diazotizing agent are fed into said reaction zone simultaneously.

12. The process of claim 11, wherein said diazotizing agent comprises dinitrogen trioxide.

13. The process of claim 11, wherein said recovery is by flashing.

14. The process of claim 10, wherein said reaction zone contains ammonium ions in said HF.

* * * * *

UNITED STATES PATENT AND TRADEMARK OFFICE
CERTIFICATE OF CORRECTION

PATENT NO. : 5,107,046
DATED : April 21, 1992
INVENTOR(S) : Gary L. Cantrell

It is certified that error appears in the above-identified patent and that said Letters Patent is hereby corrected as shown below:

Col. 4, line 1 "m" should be --$\underline{m}$-- (second and third occurences).

Col. 4, line 2 "m" should be --$\underline{m}$-- (third and fourth occurences).

Col. 4, line 5 "m" should be --$\underline{m}$-- (second occurence).

Col. 4, line 17 "m" should be --$\underline{m}$--.

Col. 4, line 18 "m" should be --$\underline{m}$--.

Col. 4, line 19 "m" should be --$\underline{m}$--.

Signed and Sealed this

Twenty-first Day of September, 1993

Attest:

BRUCE LEHMAN

Attesting Officer  Commissioner of Patents and Trademarks